United States Patent [19]

Sanders

[11] Patent Number: 4,884,575
[45] Date of Patent: Dec. 5, 1989

[54] CARDIAC PACER WITH PATIENT-CONTROLLED EXERCISE RATE AND METHOD

[75] Inventor: Richard S. Sanders, Houston, Tex.

[73] Assignee: Intermedics, Inc., Angleton, Tex.

[21] Appl. No.: 130,182

[22] Filed: Dec. 8, 1987

[51] Int. Cl.[4] .............................................. A61N 1/36
[52] U.S. Cl. ........................... 128/419 PG; 128/419 P
[58] Field of Search ...................... 128/419 PG, 419 P

[56] References Cited

U.S. PATENT DOCUMENTS

| 3,311,111 | 3/1967 | Bowers | 128/419 PG |
|---|---|---|---|
| 3,623,486 | 11/1971 | Berkovits | 128/419 PG |
| 3,693,627 | 9/1972 | Berkovits | 128/419 PG |
| 3,698,398 | 10/1972 | Berkovits | 128/419 PG |
| 4,124,031 | 11/1978 | Mensink et al. | 128/419 PG |
| 4,304,237 | 12/1981 | Mensink | 128/419 PG |
| 4,365,633 | 12/1982 | Loughman et al. | 128/419 PG |
| 4,388,929 | 6/1983 | Renine et al. | 128/419 PG |

FOREIGN PATENT DOCUMENTS 3315513 11/1983 Fed. Rep. of Germany ...... 128/421

Primary Examiner—Lee S. Cohen
Assistant Examiner—Scott Getzow
Attorney, Agent, or Firm—John R. Merkling

[57] ABSTRACT

A cardiac pacemaker pulse generator is adapted to generate electrical stimuli at a first pacing rate, and to selectively increase the rate to a second higher pacing rate. A timer triggers the rate increase to establish the higher rate as an exercise rate folliowing the passage of a preset period of time after the timer is enabled. An external magnet controlled by the patient activates a reed switch to enable the timer to commence timing. The pulse generator is further adapted to respond to a second pass of the magnet over the reed switch after enabling of the timer to thereupon disable the timer before the preset period of time has expired. If the second pass of the magnet occurs after the exercise rate has begun, the element for increasing the rate is disabled to return the pulse generator to the lower pacing rate. The change in pacing rates is made in steps.

15 Claims, 1 Drawing Sheet

CARDIAC PACER WITH PATIENT-CONTROLLED EXERCISE RATE AND METHOD

BACKGROUND OF THE INVENTION

The present invention relates generally to medical devices, and more particularly to implantable artificial cardiac pacemakers adapted to provide patient-variable stimulation rates appropriate to a condition of exercise by the patient.

The resting heart rate of sinus rhythm, that is, the rate determined by the spontaneously rhythmic electrophysiologic property of the heart's natural pacemaker, the sinus node, is typically in the range from about 65 to about 85 beats per minute (bpm) for adults. Disruption of the natural cardiac pacing and propagation system may occur with advanced age and/or cardiac disease, and is often treated by implanting an artificial cardiac pacemaker in the patient to restore and maintain the resting heart rate to the proper range.

In its simplest form, an implantable pacemaker for treatment of bradycardia (abnormally low resting rate, typically below 60 beats per minute (bpm)) includes an electrical pulse generator powered by a self-contained battery pack, and a catheter lead including at the distal end a stimulating cathodic electrode electrically coupled to the pulse generator. The lead is implanted intravenously to position the cathodic electrode in stimulating relation to excitable myocardial tissue in the selected chamber on the right side of the patient's heart. The pulse generator unit is surgically implanted in a subcutaneous pouch in the patient's chest, and has an integral electrical connector to receive a mating connector at the proximal end of the lead. In operation of the pacemaker, the electrical pulses are delivered (typically, on demand) via the lead/electrode system, including an anodic electrode such as a ring behind the tip for bipolar stimulation or a portion of the pulse generator case for unipolar stimulation, and the body tissue and fluid, to stimulate the excitable myocardial tissue.

Pacemakers may operate in different response modes, such as asynchronous (fixed rate), inhibited (stimulus generated in absence of specified cardiac activity), or triggered (stimulus delivered in presence of specified cardiac activity). Further, present-day pacers range from the simple fixed rate device that offers pacing with no sensing (of cardiac activity) function, to fully automatic dual chamber pacing and sensing functions (so-called DDD pacemakers) which may provide a degree of physiologic pacing by at least a slight adjustment of heart rate according to varying metabolic conditions in a manner akin to the natural pacing of the heart. Thus, some DDD pacemaker patients experience an increased pacing rate with physical exertion, with concomitantly higher cardiac output, and thereby, an ability to handle low levels of exercise. Unfortunately, a significant percentage of the pacemaker patient population, who suffer from atrial flutter, atrial fibrillation or sick-sinus syndrome, for example, cannot obtain the benefit of exercise-responsive pacing with conventional atrial-triggered pacemakers. Moreover, the DDD-type pacemakers are complex and costly to manufacture, which is reflected in a higher price to the patient.

It is a principal object of the present invention to provide a relatively simple and inexpensive pacemaker which provides pacing at a desired resting rate, and which is subject to limited control by the patient to provide a desired exercise rate for a preset period of time following which the pacemaker returns to the resting rate.

Various types of rate responsive pacemakers have been proposed which would sense a physiological parameter that varies as a consequence of physical stress, such as respiration, blood oxygen saturation or blood temperature, or merely detect physical movement, and correspondingly adjust the pacing rate. Many of these rate responsive pacemakers may also be relatively complex, and therefore expensive to the patient.

The present invention is directed toward a low cost pacemaker which can be adjusted at will by the patient, subject to the limited amount of control programmed into the device by the physician for that patient. According to the invention, patient control is manifested by bringing an external magnet into proximity with an implanted reed switch associated with the pacemaker. Of course, limited magnet control has been afforded to the patient in the past for some purposes, such as to enable transtelephonic monitoring of the pacemaker functions. Also, techniques are presently available which permit external adjustment of the stimulation rate of the pacemaker after implantation, as by means of a programming unit available to the physician. For obvious reasons, it is undesirable to give the patient the same latitude to control his pacemaker.

In U.S. Pat. No. 3,623,486, Berkovits disclosed a pacemaker adapted to operate at either of two stimulation rates, and switchable from one to the other by the physician using an external magnet. In this manner, the physician would be able to control the pacer mode and rate according to the needs of the particular patient. The purpose, in part, was to provide a pacemaker which had some adaptability to the patient's requirements. However, once set by the physician, the selected resting rate was maintained for that patient by the implanted pacer.

Another technique for external adjustment of pacing rate by the physician is found in the disclosures of U.S. Pat. No. 3,198,195 to Chardack, and U.S. Pat. No. 3,738,369 to Adams et al. In each, rate control is exercised by inserting a needle through a pacemaker aperture beneath the patient's skin to adjust a mechanism. In the Adams et al. disclosure, the needle is used to change the position of a magnet within the paper to actuate a rate-controlling reed switch.

In U.S. Pat. No. 3,766,928, Goldberg et al. describe an arrangement for continuous adjustment of rate by a physician using an external magnet that cooperates with a magnet attached to the shaft of a rate potentiometer in the implanted pacemaker, to provide the initial setting of pacing rate desirable for the particular patient.

More recent proposals offer the patient limited control over the pacing rate. In U.S. Pat. No. 4,365,633, Loughman et al. disclose a pacemaker programmer which is conditioned by the physician to give the patient the capability to select any of three distinct rates: for sleep, for an awake resting state, and for exercise. The programmer generates a pulsating electromagnetic field, and allows the patient to select any of those three modes with an abrupt change in rate when the coil pod of the programmer is positioned over the implanted pacemaker. It is, of course, necessary to have the programmer at hand in order to change the stimulation rate, and the use of the device in public can be a source of extreme embarrassment to the patient.

In U.S. Pat. No. 4,545,380, Schroeppel describes a technique for manual adjustment of rate control contrasted with the activity sensing, automatic rate control disclosed by Dahl in U.S. Pat. No. 4,140,132. According to the Schroeppel patent, a piezoelectric sensor and associated circuitry are combined with the implanted pulse generator of the pacemaker to allow the patient to change from a resting rate to a higher rate by sharp taps on his chest near the site of the piezoelectric sensor. Such an arrangement requires that the sensor be sufficiently sensitive to respond to the patient's sharp taps, and yet be insensitive to the everyday occurrences the patient encounters while undergoing normal activities and which could otherwise result in false triggerings. These include presence in the vicinity of loud noise such as is generated by street traffic, being jostled in a crowd, experiencing bumps and vibrations while riding in a vehicle, and the like. Further, even when controlled in the manner described, this type of switching results in an abrupt, non-physiological change of rate.

Accordingly, it is another object of the present invention to provide a pacemaker which is capable of being controlled externally by the patient to assume exercise and non-exercise rate modes, in a manner that allows discreet and yet reliable control.

Yet another object of the invention is to provide a cardiac pacemaker whose stimulation rate is controllable by and according to a schedule selected by the patient.

SUMMARY OF THE INVENTION

Briefly, according to the present invention a cardiac pacemaker is manually controllable by the patient to preset time intervals of operation at a relatively high (exercise) rate and lower (resting) rate according to the patient's own predetermined schedule of exercise and rest. An important aspect of the invention is that the pulse generator may be implemented to undergo an adjustment of stimulation rate from a fixed resting rate of, say, 75 bpm, to a preselected exercise rate of, say, 120 bpm, following a predetermined period of time after activation by the patient using an external magnet, that is, after a predetermined delay following a patient-initiated command signal, and to remain at the higher rate for a preselected time interval. Thus, the patient may effectively "set a clock" in his pacemaker to elevate his heart rate at the time and for the duration of a scheduled exercise session, such as a game of tennis. Moreover, he may activate the pacemaker in this manner in the privacy of his own home well in advance of the exercise session.

According to another aspect of the invention, the pulse generator is implemented to return automatically to the resting rate at the expiration of the preselected exercise rate time interval. Hence, the patient need not carry his magnet with him to readjust the pacer to the resting rate at the completion of the scheduled exercise session. According to this aspect, after operating at the elevated stimulation rate for a time interval preselected to be suitable for the exercise session, say, one hour, the generator resets itself to return to the initial resting rate.

According to another feature of the invention, the rate is incremented and decremented in steps from one rate setting to the other to avoid abrupt changes, and therefore to provide a more physiological rate control than has heretofore been available in manually controlled pacemakers.

A further feature of the invention is that the pulse generator may be activated to disable the exercise rate command at any time after it has been given, including that to produce an early conclusion to an already-commenced exercise session. For example, if a scheduled tennis game or bicycling run is called off by the patient's partner after the patient has programmed in the higher rate, he need merely apply the magnet in proximity to the implanted pulse generator again to cancel the previous command and maintain the fixed resting rate. Similarly, if the exercise session is shortened, the rate may be returned to the resting rate by simply applying the magnet over the pulse generator.

BRIEF DESCRIPTION OF THE DRAWINGS

The above and still further objects, aspects, features and attendant advantages of the present invention will become apparent to those of ordinary skill in the field to which the invention applies from a consideration of the following detailed description of a preferred embodiment thereof, taken in conjunction with the accompanying drawing, in which.

DETAILED DESCRIPTION OF A PREFERRED EMBODIMENT

Figure 1:
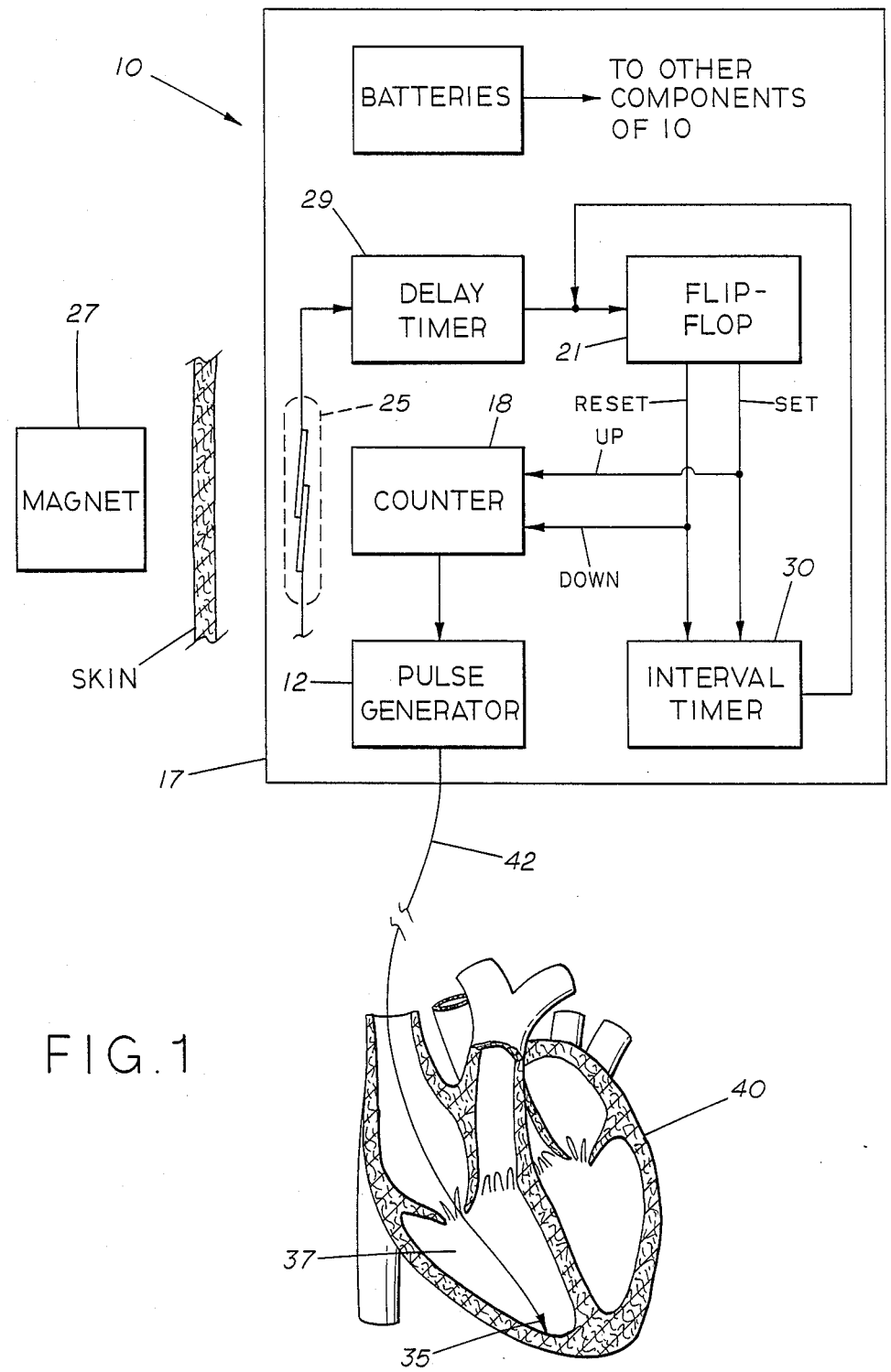
FIG. 1 is a block circuit diagram of a pulse generator unit of a cardiac pacemaker according to a preferred embodiment of the invention.

Referring now to FIG. 1, an implantable pulse generator unit 10 includes a pulse generator 12 and batteries 15 housed in a biocompatible metal case 17. Pulse generator 12 is implemented to be rate limited to generate output pulses at rates up to either of two low/high limit rates—for example, 75 pulses per minute (ppm) and 120 ppm, respectively—and to be incremented from the lower rate to the higher rate and decremented from the higher rate to the lower rate under the control of an up/down counter 18 associated with the pulse generator 12 in unit 10. Counter 18 may be set by application of a voltage level to its "up" input to commence counting toward the higher rate, and thereby to incrementally step the pulse repetition frequency up to that rate, and may be reset by application of a voltage level to its "down" input to commence counting toward the lower rate, and thereby decrementally step the pulse repetition frequency down to that rate. This is accomplished under the control of set and reset output voltage levels generated by a flip-flop circuit 21 also housed in case 17. The pulse generator unit 10 also includes a reed switch 25 which is actuable by placement of a magnet 27, external to the skin of the patient in whom the unit 10 is implanted, in proximity to case 17.

Reed switch 25, when actuated, serves to enable a delay timer 29 in unit 10. The delay timer responds to the enabling input to commence timing of its preset time delay interval. At the end of the delay interval, delay timer 29 produces a pulse for application to the flip-flop 21. Subsequent actuation of the reed switch before the timer 29 has timed out serves to disable the timer and reset it in preparation for a subsequent enabling signal from the reed switch. If timer 29 has already timed out before the reed switch is again actuated, the timer will respond to the disabling input, when the reed switch is actuated, to produce another pulse for application to the flip-flop 21. The flip-flop is thereupon reset and produces its reset output voltage level.

The set and reset output voltage levels of flip-flop 21 are also applied respectively to "set" and "reset" inputs of an interval timer 30. Upon being set, the interval timer commences timing out a predetermined time interval, and, at the expiration of that interval, generates a pulse for application to flip-flop 21. Upon being reset, the interval timer 30 is returned to the start of the predetermined time interval in preparation for initiating the timing of that interval on receipt at its "set" input of the next set output voltage level from the flip-flop.

The preset time period of delay timer 29 and the predetermined time interval of interval timer 30 are programmable by the physician according to the desires and needs of the particular patient. If, for example, the patient has a regularly scheduled early morning brisk walking session of one hour with friends, and resides near the starting point of the walk, the time period of the delay timer 29 may be programmed to be fifteen minutes. The time interval of the interval timer 30 is programmed to be one hour in length.

In operation, the pulse generator produces output pulses at the resting rate prescribed (and programmed) by the physician for the particular patient—in this exemplary embodiment, a resting rate of 75 bpm. The pulses are delivered to the stimulating cathodic electrode 35 in the right ventricle of the heart 40 via a lead 42, the reference electrode (anode) and the body tissue and fluids, according to the mode in which the pacemaker is designed to operate.

In the preferred embodiment, the pacemaker continues to operate at that rate unless and until the patient elects to initiate the exercise rate cycle. To do so, the patient places the magnet 27 in proximity to the implanted pulse generator unit 10 at about fifteen minutes prior to the appointed time for the exercise session, as a command to actuate reed switch 25. The patient may then choose to leave the magnet at home or take it along in the glove compartment of his car, since actuation of the reed switch has enabled the delay timer 29 and nothing more need be done by the patient to enable the pacemaker to commence the exercise rate at the expiration of the preset delay period.

Before the end of that period the patient has arrived at the starting point for the exercise session, and at the end of the delay period, the delay timer applies a pulse to flip-flop 21 which responds by generating a set output voltage level. The set voltage is applied to both the "up" input of counter 18 and the "set" input of interval timer 30. Accordingly, the counter commences its count, preferably at a relatively slow rate of, say, ten counts per minute, and correspondingly incrementally steps the pulse generator 12 output rate up to the upper rate limit of 120 ppm, and thereby gradually increases the patient's heart rate from 75 bpm to 120 bpm as the patient commences to exercise. Hence, the patient's heart rate and cardiac output are now at levels adequate for the patient to carry out the exercise session.

The pulse generator continues to supply pulses at the upper rate limit until interval timer 30, which commenced its predetermined time interval with the application of the set input voltage, times out, whereupon the interval timer produces an output pulse which is applied to flip-flop 21 to reset the latter. The flip-flop responds by providing a reset output voltage level for application to the "down" input of counter 18 and the "reset" input of the interval timer. Accordingly, the counter decrementally steps the pulse repetition frequency of the pulse generator down, preferably at the ten pulses per minute rate, to the lower rate limit of 75 ppm corresponding to a heart rate of 75 bpm. In this manner, the patient's heart rate is reduced gradually from the exercise rate to the resting rate at a time commensurate with the end of the exercise session. Also, the resetting of the interval timer by the set output voltage level of the flip-flop assures that the timer is ready to commence timing its predetermined interval on receipt of the next "set" input.

In the event that the exercise session is called off at any time after the delay timer 29 has been enabled and before the interval timer has timed out, the patient need merely place the magnet 27 once again in proximity to the implanted pulse generator unit. If the delay timer has not yet timed out, it is disabled by the actuation of the reed switch, and hence, flip-flop 21 remains reset, interval timer 30 remains reset, counter 18 is at its low count, and pulse generator 12 is at its lower rate limit. If the delay timer has timed out, it produces an output pulse in reponse to the disabling input from the reed switch, thereby resetting the flip-flop, resetting the interval timer, returning counter 18 toward its low count and pulse generator 12 toward its lower rate limit. To that end, delay timer 29 is provided with an internal clock such that, once enabled to time out the delay interval, it cannot be again enabled to do so until the passage of a preselected time interval, which is one hour and fifteen minutes in the present example, unless it has first been disabled during that overall interval. Of course, to cancel the exercise rate, the patient must have the magnet available to issue the second command but, as previously noted, once the delay timer is enabled through actuation of the reed switch the magnet may be kept in a convenient location, such as the glove compartment of the patient's car, to allow cancellation of the exercise rate in private.

Although a presently preferred embodiment has been described herein, it will be evident to those skilled in the art that variations and modifications of the preferred embodiment may be carried out without departing from the spirit and scope of the invention. Accordingly, it is intended that the present invention shall be limited only to the extent required by the appended claims and the applicable rules of law.

What is claimed is:

1. In combination with an implantable cardiac pacemaker for delivering electrical stimuli to the heart of a patient to pace the heart rate, said pacemaker comprising:
pulse generator means for selectively producing said electrical stimuli at a fixed resting rate and at a higher exercise rate,
lead means associated with said pulse generator for delivering said stimuli to a selected chamber of the heart, and
timer means for stepping-up said pulse generator means from said resting rate to said exercise rate after an adjustable preset delay following activation of said timer means, said preset delay being of a duration perceptible by the patient; and
external control means for patient initiation of a first command to said pacemaker to activate said timer means.

2. In combination with an implantable cardiac pacemaker for delivering electrical stimuli to the heart of a patient to pace the heart rate, said pacemaker comprising:
pulse generator means for selectively producing said electrical stimuli at a fixed resting rate and a higher exercise rate, lead means associated with said pulse generator for delivering said stimuli to a selected chamber of the heart, and delay means for stepping-up said pulse generator means from said resting rate to said exercise rate after an adjustable preset delay following activation of said delay means, means associated with said pulse generator means and said delay means for maintaining said exercise rate for a predetermined time interval following said preset delay and then returning said pulse generator means to said resting rate; and an external control means for patient-initiation of a command to said pacemaker to activate said delay means.

3. The combination according to claim 2, wherein said delay means is responsive to a second command initiated by the patient from said external control means at any time after receipt of the first said command and before the expiration of said predetermined time interval, to cancel the activation of said delay means.

4. The combination according to claim 3, wherein the stepping up and returning of said rates at which said stimuli are produced by said pulse generator means is effected gradually.

5. An implantable pulse generator unit for a cardiac pacemaker for use with an external magnet to permit patient-initiated adjustment of pacing rate from a resting rate to an exercise rate and vice versa, said unit comprising:

generator means for generating electrical stimuli at said resting rate, control means associated with said generator means responsive, when enabled, for controllably increasing the rate at which electrical stimuli are generated from said generator means from said resting rate to said exercise rate, and timer means responsive to positioning of said external magnet in proximity to said pulse generator unit for enabling said control means an adjustable preset delay period after said positioning, said preset delay period being of a duration perceptible to the patient.

6. An implantable pulse generator unit for a cardiac pacemaker for use with an external magnet to permit patient-initiated adjustment of pacing rate from a resting rate to an exercise rate and vice versa, said unit comprising:

generator means for generating electrical stimuli at said resting rate, control means associated with said generator means responsive, when enabled, for controllably increasing the rate at which electrical stimuli are generated by said generator means from said resting rate to said exercise rate, said control means including timing means for maintaining the rate at which electrical stimuli are generated by said generator means at said exercise rate for a predetermined time interval; and delay means responsive to positioning of said external magnet in proximity to said pulse generator unit for enabling said control means an adjustable preset delay period thereafter.

7. The pulse generator unit of claim 6, wherein said control means automatically returns said generator means to said resting rate following the expiration of said predetermined time interval.

8. The pulse generator unit of claim 7, wherein said control means gradually increases the rate at which electrical stimuli are generated by said generator means from said resting rate to said exercise rate, and gradually returns said generator means to said resting rate following the expiration of said predetermined time interval.

9. The pulse generator unit of claim 6, wherein said delay means is responsive to a repositioning of said external magnet in proximity to said pulse generator unit after said control means has been enabled, for disabling said control means.

10. A cardiac pacemaker pulse generator for generating electrical stimuli to be delivered to the heart of a patient to pace the heart rate, said generator comprising:

means for generating said electrical stimuli at a first pacing rate, means electrically connected to said stimuli generating means for selectively increasing the rate at which said stimuli are generated to a second higher pacing rate, timing means for triggering said rate increasing means to increase said first pacing rate to a second higher pacing rate upon passage of an adjustable preselected period of time after said timing means is enabled, said preselected period of time being of a duration perceptible by the patient, means responsive to a command signal from a patient-activated external device for enabling said timing means to commence timing.

11. The pulse generator according to claim 10, wherein said enabling means is further responsive to a second command signal after said timing means is enabled, to disable said timing means prior to passage of said preselected period of time.

12. The pulse generator according to claim 10, further including means responsive to a second command signal while said stimuli are being generated at said second higher pacing rate, for disabling said rate increasing means and thereby returning the rate at which said stimuli are generated by said stimuli generating means to said first pacing rate.

13. The pulse generator according to claim 12, wherein said rate increasing means is responsive, when disabled, to decrementally reduce the rate at which said stimuli are generated by said stimuli generating means.

14. The pulse generator according to claim 10, wherein said rate increasing means is responsive to said timing means reaching preset time intervals toward passage of said preselected period of time, for incrementally increasing the rate at which said stimuli are generated by said stimuli generating means in steps as each preset time interval is reached.

15. The method of pacing a pacemaker patient's heart rate using a magnet-controlled implantable pulse generator to adjust the stimulation rate from a resting rate to an exercise rate and vice versa, comprising the steps of maintaining the stimulation rate of said pulse generator at said resting rate, initiating a command signal to reset the stimulation rate of said pulse generator to said exercise rate after an adjustable programmed delay period following said command signal, and returning the stimulation rate of said pulse generator to said resting rate in increments following a predetermined interval of time at said exercise rate.

* * * * *